(12) United States Patent
Pageat

(10) Patent No.: US 7,723,388 B2
(45) Date of Patent: May 25, 2010

(54) AVIAN APPEASING PHEROMONES TO DECREASE STRESS, ANXIETY AND AGGRESSIVENESS

(75) Inventor: Patrick Pageat, Route de Saint-Saturnin (FR)

(73) Assignee: Fideline, St. Saturnin d'Apt (FR)

( * ) Notice: Subject to any disclaimer, the term of this patent is extended or adjusted under 35 U.S.C. 154(b) by 1358 days.

(21) Appl. No.: 11/007,584

(22) Filed: Dec. 9, 2004

(65) Prior Publication Data

US 2005/0143465 A1   Jun. 30, 2005

Related U.S. Application Data

(63) Continuation of application No. PCT/EP03/07144, filed on Jun. 19, 2003.

(60) Provisional application No. 60/389,768, filed on Jun. 19, 2002.

(30) Foreign Application Priority Data

Jun. 19, 2002   (EP) .................................. 02291533

(51) Int. Cl.
*A61K 31/202* (2006.01)
*A01K 31/19* (2006.01)

(52) U.S. Cl. .................... 514/560; 424/442; 119/300

(58) Field of Classification Search .................. None
See application file for complete search history.

(56) References Cited

U.S. PATENT DOCUMENTS 3,714,682 A * 2/1973 Harben, Jr. .................. 452/115
5,662,921 A * 9/1997 Fein et al. .................... 424/436
5,776,363 A * 7/1998 Hornung et al. ........ 252/299.01
6,077,867 A * 6/2000 Pageat ......................... 514/558
6,169,113 B1   1/2001 Pageat
6,384,252 B1 * 5/2002 Pageat ......................... 554/223
6,951,658 B1 * 10/2005 Pearson et al. .............. 424/520
2001/0027952 A1 * 10/2001 Ciancaglini et al. ......... 210/660

FOREIGN PATENT DOCUMENTS

EP   0 948 963 A   10/1999

OTHER PUBLICATIONS

Kolattukudy, et al., "Disappearance of short chain acids from the preen gland of male mallard ducks during eclipse," Journal of Lipid Research, 26:898-994 (1985).*

Kolattukudy, et al., "Estradiol induces proliferation of peroxisome-like microbodies and the production of 3-hydroxy fatty acid diesters, the female pheromones, in the uropygial glands of male and female mallards," Journal of Biological Chemistry, 266(15):9795-9804 (1991).*

Bohnet et al., "Estradiol Induces Proliferation of Peroxisome-Like Microbodies and the Production of 3 Hydroxy Fatty Acid Diesters the Female Phermomones in the Uropygial Glands of Male and Female Mallards," *Journal of Biological Chemistry*, vol. 266, No. 15, pp. 9795-9804 (1991).

* cited by examiner

*Primary Examiner*—Shanon A Foley
(74) *Attorney, Agent, or Firm*—Venable LLP; Michael A. Gollin; Nancy J. Axelrod

(57) ABSTRACT

Compositions comprising a mixture of fatty acids or derivatives thereof derived from secretions of the uropygial glands of birds are disclosed. This composition, named an avian appeasing pheromone, can be used to decrease stress, anxiety and agressiveness in birds.

23 Claims, 11 Drawing Sheets

*p<0.01; **p<0.01

AVIAN APPEASING PHEROMONES TO DECREASE STRESS, ANXIETY AND AGGRESSIVENESS

The present invention relates to a composition comprising a mixture of fatty acids or derivatives thereof derived from secretions of the uropygial glands of birds. This composition, named an avian appeasing pheromone, can be used to decrease stress, anxiety and aggressiveness in birds.

BACKGROUND OF THE INVENTION

Stress, by definition is the reaction of an animal body to forces of deleterious nature, infections and various abnormal states that tend to disturb homeostasis.

Animals exposed to stress respond with changes in the activity of the autonomic and neuroendocrine systems and in behavior. The activation of these biological systems is a prerequisite for the animal to cope with stress and thus is the principal resource that will provide the adequate biological defense against a threat that challenges the homeostasis of the animal. Moberg, G.P. Animal Stress, pp. 27-49 (1985); Vogel, W. H. Neuropsychobiology, 13 p. 1290 (1985).

Stress is associated with an objective aggression and the consequences appear in altering different systems such as humoral, metabolic, immunolgic and/or behavioral systems. The hormonal response is traditionally determined by a release of cortisol, a decrease in the secretion of growth hormone and an increase in thyroid hormones and also the sexual steroids. Stress also has a role for diminishing either directly or indirectly the amount of consumption, which is a principal problem with animal breeders. This decrease in the amount of consumption in animals can be caused either by an increase in metabolism or a decrease in food consumption due to stress.

More specifically, stress can be observed by examining several clinical elements in the blood. It is known that in a stressed condition an increase in the ratio of H/L (heterophiles/lymphocytes; heterophiles meaning all white blood cells that are not lymphocytes in avians) and an augmentation in the level of hormones such as circulating T4 (thyroxine), cortisol and prolactin. Davis and Siopas, *Poultry Science*, 66, pp. 34-43 (1987).

The augmentation of T4 in avians results in the alteration of different well known physiological conditions such as an increase in the level of carbohydrate catabolism, a deregulation of thermoregulation, an increase in heartbeat and an increase in urine and fecal calcium. Idelman, *Col. Grenoble Science* PUG (1990).

Physiological stressors can also result in an abnormally elevated corticosterone secretion. Campo J.L., S. G. Davila,. *Poult. Sci.* 81: 1637-1639. (2002); Moberg G. P.,. In: The Biology of animal stress (Moberg & Mench Ed.), CABI, 1-23(2000)

Besides physiological tests, behavioral tests can also be performed to evaluate stress and/or fear in avians. One of the most utilized behavioral tests is the test of Tonic Immobility (TI) as described by Campo J. L., S. G. Davila,. *Poult. Sci.* 81: 1637-1639 (2002).

It can be appreciated that the change in the physiological conditions due to stress in avians can result, in some instances, in dire effects such as mortality and in many instances loss of weight. Moreover, stress can cause behavioral changes which results in aggressiveness such as pecking other birds, cannibalism, and causing damage to the skin in avian settings. Stress is a real detriment to the aviculturist, since it results in less production of the avian.

Therefore a reduction in stress in birds and especially in avian breeding would lead to less mortality, more weight gain and higher quality production resulting in greater financial gain to the aviculturist.

The advantages resulting from a reduction for in stress in avians are extremely beneficial for those aviculturists who use confinement housing. In confinement housing a large number of avians are raised in cages in hen houses and there are a. large number of birds per cage. Since the avians are confined in a small area with other avians, the stress levels are higher in comparison to those avians that are raised in a free range system. Stress in avians in confinement housing systems can therefore lead to a large loss of yield (Craig J. V., and W. M. Muir, *Poult. Sci.* 75: 294-302.(1996) due to feather pecking behavior (Kjaer J. B., and P. Sorensen,. *Br. Poult. Sci.* 38: 333-341 (1997) higher feed to gain ratio (Buitenhuis A. J. et al. $7^{th}$ WCGALP, Montpellier-France, communication n° 14-06) higher mortality (Buitenhuis A .J., et al $7^{th}$ WCGALP, Montpellier-France, communication n° 14-06) or/and poor meat (carcass) quality (Tankston J. D. et al. *Poult. Sci.* 80: 1384-1389 (2001).

In a confinement housing system, the birds remain indoors and are provided with light twenty-four hours a day to encourage feed consumption. Litter is generally spread on the floor in the hen houses which acts to absorb moisture, dilute manure and provides cushioning and insulation for the birds. In the conventional industry, litter is spread 2 to 4 inches deep and maintained at a 20% to 30% moisture content. There is generally a rest period of about a week between flocks, when the hen houses are cleaned out of de-caked.

By definition, pheromones are substances released by the body that cause a predictable reaction by another individual of the same species.

A number of different glands are known to produce pheromones in male mammals such as the submaxillary salivary glands, the parathyroid glands and the sebaceous glands.

Pheromones that are secreted in submaxillary salivary and parathyroid glands in males, are used to mark females during courtship. In boars, the secretion of these glands results in agnostic behavior. These secretions are known to contain a mixture of androstenol and andosterone.

It is known in the art that pheromones in mammals can be used to reduce stress, anxiety and aggressiveness as demonstrated in U.S. Pat. Nos. 6,077,87, 6,054,481 and 6,169,113. These pheromones were derived from secretions of mammalian mammary glands. However, mammary glands do not exist in birds. Moreover, there are some doubts among specialists about the presence of pheromones in birds since there is no vomeronasal organ, which is a sensory organ with its own pathway to the brain.

The uropygial glands in birds are a bibbed holocrine gland with secretions that form several functions in birds. These functions include waterproofing the feathers, manufacturing of vitamin D precursors, keeping the bill, skin and feathers supple and preventing bacterial infection. The secretions of the uropygial gland are generally spread over the feathers during the act of preening and thus weatherproofs the feathers.

Bohnet et al in the Journal of Biochemistry vol. 226, No. 15 pp. 9795-9804 (1991) describe the production in female mallards of sex pheromones, diesters of 3-hydroxy fatty acids in their uropygial glands during the mating season. Outside the mating season the uropygial gland only produced a usual monoester wax. It is not known how the uropygial gland switches its biological processes to produce sexual pheromones during the mating season only.

The sexual pheromones as described by Bohnet et al, supra and known to be produced in various birds only during mating season act as attractants or sexual stimulants and cannot be used as appeasing pheromones which act to calm, sooth or relieve anxiety due to stress as in the present invention. Moreover, the chemical composition of sexual pheromones is different than the avian appeasing pheromones of the present invention.

Thus, an aspect of the present invention is to provide an avian appeasing pheromone derived from the uropygial gland of an avian.

In another aspect the present invention provides a composition comprising an avian appeasing pheromone comprising lauric acid, palmitic acid, linoleic acid and oleic acid and/or derivatives thereof and/or isomers thereof, as well as mixtures of one or more of these fatty acids with one or more of their derivatives and/or one or more of their isomers.

In yet another aspect, the present invention provides a composition comprising an avian appeasing pheromone comprising a mixture of about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

In yet another aspect the present invention provides a process to treat stress in an avian, said process comprising administering to an avian in need of such treatment an avian appeasing pheromone derived from secretions around the uropygial gland of an avian.

In yet another aspect the present invention relates to a process of treating weight loss in an avian, said process comprising administering to an avian in need of such treatment an avian appeasing pheromonal composition derived from secretions around the uropygial gland of an avian.

In yet still another aspect the present invention provides a process of treating a domestic avian during transportation to eliminate their anxiety, said process comprising administering to an avian in need of such treatment an avian appeasing pheromonal composition derived from secretions around the uropygial gland of an avian.

In another aspect the present invention provides a process to improve feed conversion in an avian comprising administering to an avian in need of such treatment an avian appeasing pheromonal composition derived from secretions around the uropygial gland of an avian.

These and other objects are achieved by the present invention as evidenced by the summary of the invention, description of the preferred embodiments and the claims.

SUMMARY OF THE INVENTION

The present invention provides a composition comprising an avian appeasing pheromone derived from around the uropygial gland of an avian.

In one aspect of the invention the present invention discloses a composition comprising an avian appeasing pheromone comprising lauric acid, palmitic acid, linoleic acid and oleic acid and/or derivatives thereof and/or isomers thereof, as well as mixtures of one or more of these fatty acids with one or more of their derivatives and/or one or more of their isomers.

In another aspect the present invention provides a composition comprises an avian appeasing pheromone comprising about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

The derivatives of the present invention include esters such as methyl esters, salts, alcohols, ketones, ethers, aldehydes, sterols and amides of lauric acid, palmitic acid, linoleic acid and oleic acid.

Solutions containing the above compositions are also contemplated by the present invention.

In another aspect the present invention provides a process for the treatment of stress in an avian said process comprising administering to an avian in need of such treatment a composition comprising an avian appeasing pheromone derived from secretions around the uropygial gland of an avian.

In yet another aspect the present invention discloses a process of treating weight loss in an avian, said process comprising administering to an avian in need of such treatment an avian appeasing pheromonal composition derived from secretions around the uropygial gland of an avian.

In still another aspect the present invention provide a process of treating a domestic avian during transportation to eliminate their anxiety, said process comprising administering to an avian in need of such treatment an avian appeasing pheromonal composition derived from secretions around the uropygial gland of an avian.

In yet another aspect the present invention discloses a process to improve feed conversion in an avian comprising administering to an avian in need of such treatment an avian appeasing pheromonal composition derived from secretions around the uropygial gland of an avian.

DESCRIPTION OF THE PREFERRED EMBODIMENTS

Figure 1:
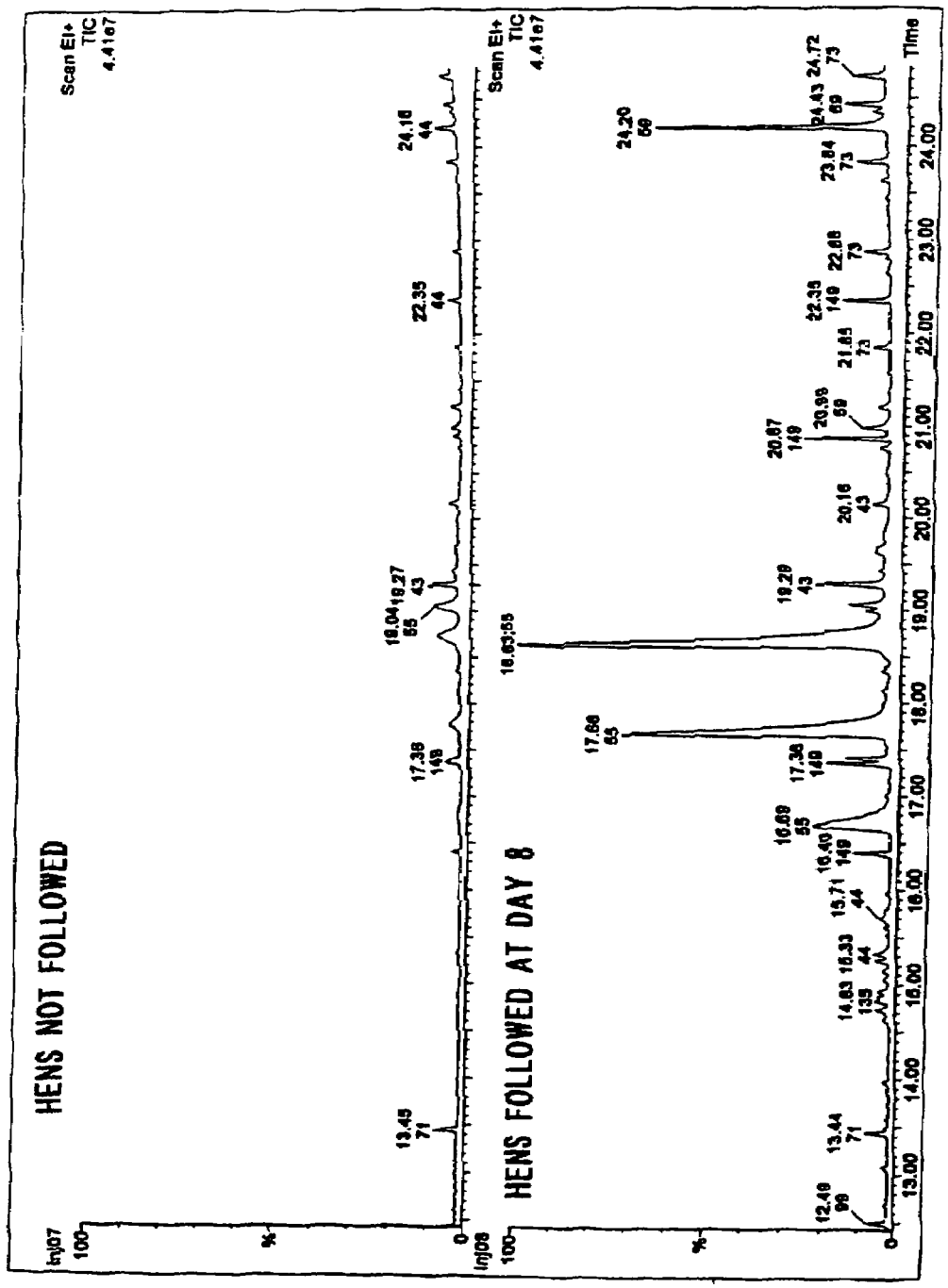
FIG. 1 are gas chromatograph/mass spectroscopy spectrum profiles of hens that were not followed by their chicks and hens that were followed by the chicks at day 8.

As used herein, the word "bird" and "avian" (or avians) are used interchangeably and encompass any warm-blooded animal with feathers and wings, that lays eggs and is usually able to fly. Examples of birds, include, but are not limited to chicks, chickens, guinea hens, parrots, turkeys, hens, ducks, geese and the like.

As used herein the word "stress" is meant the reaction of an animal body to forces of deleterious nature, infection and various abnormal states that tend to disturb homeostasis. This reaction may be a physical reaction or an emotional reaction including anxiety.

By "anxiety" is meant an apprehension of anger and dread accompanied by restlessness, tension and the like, which is a reactional status characterized by a high probability to provide behavioral and emotional responses of fright. In neurophysical terms, this anxious state is accompanied by an hyperactivity of the noradrenergic and serotonin systems.

By "pheromone" is meant a substance released by the body of a particular species that causes a predictable reaction by another individual of the same species, which substance may serve, for example, as a specific attractant, social communicator, sexual stimulant and the like.

By "appeasing pheromone" is meant a pheromone that calms, soothes or relieves stress, anxiety and aggressiveness. Appeasing pheromones should be distinguished from sexual pheromones, the latter that act as either sexual stimulants or attractants.

By "stress-associated diseases" is meant any disease whose symptoms increase due to stress.

By "improved feed conversion" means the reduction of the ratio in food consumption/weight gained.

By the term "solution" is meant a solid that is dispersed through a liquid either by being dissolved in it or being in suspension.

By "appeasing effect" is meant a reduction of fear. Apprehension, anxiety, as well as the behavioral and physical consequences associated with stress. The behavioral consequences associated with stress include tremor, vocalization, flight, aggression, displacement activities and the like. The physical consequences associated with stress include changes in heart rate, changes in levels of epinephrine, norepinephrine, ACTH, cortisol glucose and the like. In avians used as a source of food, this definition includes husbandry parameters such as growth weight, food conversion efficiency, quality of the meat, bacterial quality of the products such as a lack of Salmonella, and quantity of eggs produced. It also includes quality of the feathers produced by birds and quality of goose down.

By "enhancer composition" is meant an active pheromonal composition that is species-species specific in birds and which can be used to enhance or act synergistically with the basic pheromonal composition to increase the effectiveness in specific species of the composition.

By "heterophile" is meant all white blood cells that are not lymphocytes that are found in avians.

As used herein the term "isomers" includes structural isomerism and spatial isomerism and refers to the isomers of the fatty acids of lauric acid, palmitic acid, linoleic acid and oleic acid, as well as their derivatives.

When referring to the mixtures of one or more of the fatty acids of the present invention with one or more of their derivatives and/or one or more of their isomers means that the composition can include, for example only, lauric acid, a derivative of palmitic acid, an isomer of linoleic acid and an isomer of a derivative of oleic acid. It will be appreciated that the compositions of the present invention encompass all of the permutations (and not only that exemplified above) of the mixtures of the disclosed fatty acids with their derivatives and/or isomers thereof. Furthermore, the derivatives and isomers referred to herein have the same weight percentages as their fatty acid counterparts. For example a derivative, isomer or derivative of an isomer for lauric acid should have a concentration between 12.3 to 13.7 (w %/w %).

More specifically, the present invention relates to the identification of an avian appeasing pheromonal composition that is derived from secretions around the uropygial gland of birds.

The compositions of the present invention are appeasing and pheromonal in origin and are made up of volatile molecules, the essential components of these molecules being amines and fatty acids from indolic derivatives, as well as esters of these amines and fatty acids.

The composition of the present invention comprises a mixture of lauric acid, palmitic acid, linoleic acid and oleic acid and/or derivatives thereof and/or isomers thereof, as well as mixtures of one or more of these fatty acids with one or more of their derivatives and/or one or more of their isomers.

More specifically, the basic composition of the present invention comprises a mixture of about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

The composition can also be attached to a chemical carrier provided that the bioactive structure of the fatty acids is preserved. Such carrier molecules include, but are not limited to, resins, liposomes, crown compounds, carrier proteins, polymers and the like.

The fatty acids can be used in their pure form, i.e., as a free fatty acid, as well as their derivative form such as esters of fatty acids or salts of fatty acids, as well as alcohols of fatty acids, ketones of fatty acids, ethers of fatty acids and amides of fatty acids. These fatty acid derivatives can replace one or more or all of the fatty acids in the compositions of the present invention and have the same effects. The derivatives of the fatty acids can be found in the compositions or in the solutions of the present invention.

The composition has been found to have an appeasing effect in avians and can be used to relieve stress, anxiety, reduce aggressive behavior, enhance weight gain and enhance egg production.

An enhancer composition containing between 5% to 35% (w %/w %) can also be added to the avian appeasing pheromone composition, if desired. This enhancer composition comprises volatile organic compounds and mixtures thereof. This enhance composition may be species-specific in nature and may vary according to the avian species selected for use in the present invention.

The compounds that can be used in the enhancer composition, include, but are not limited to, amines and fatty acids from indolic derivatives, esters of these amines and fatty acids, ketones such as acetone, alcohols, sterols and the like.

Nontoxic fillers can also be added to the composition, which include fatty acids, alcohols, amines, squalene and glycerol.

In another aspect the present invention comprises the avian appeasing pheromonal composition in solution.

The present invention thus provides a solution of lauric acid, palmitic acid, linoleic acid and oleic acid and/or derivatives thereof and/or isomers thereof, as well as mixtures of one or more of these fatty acids with one or more of their derivatives and/or one or more of their isomers.

Thus, in another aspect the present invention provides in solution about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

The composition may be in the form of a solution, aerosol spray, gel, slow release matrix, shampoo and the like. The composition can also be placed in liposomes, in a diffuser, in polymers, is in an electric diffuser and be microencapsulated.

The concentration of the above-mentioned fatty acids may vary depending upon the final form of use. However, the concentrations of the specific fatty acids that are utilized and their concentration may be ascertained and tested according to the methods set forth in the present invention.

The fatty acids, which are generally solid in nature, can be diluted in any nonaqueous solvent to form the solution of the present invention. Solvents such as propylene glycol, alcohol, ether, chloroform, ethanol, benzene, carbon disulfide, polysorbate, propyl alcohol, isopropanol, 2-propanol, fixed and volatile oils and the like. Combinations of these solvents can also be used.

Thus a combination of propylene glycol and absolute ethanol can be used as a solvent in the present invention. 90% to 98% propylene glycol and 2% to 10% absolute ethanol is set forth as an example. 5% to 40% isopropanol and 60% to 95% propylene glycol can also be used.

Fatty acids are commercially available from various chemical companies in solid form. However, since it is difficult to solubilize fatty acids, the fatty acid is generally added to the solvent under constant agitation and at a temperature of between 37° C. to about 38° C. 37.5° C. can also be used.

Once obtained, the compositions of the present invention can be tested for their efficacy to prevent stress in an avian. Well documented stressors are, for example, the weaning of birds, the transportation of birds, and the like. Application of the present compositions of the invention in the form of a spray, aerosol and the like in the area surrounding the stressful events results in diminution of stress as indicated by a variety of factors such as weight gain, social behavior with respect to other birds, wounds on the body, salivary cortisol and the like.

Thus, the compositions of the present invention can be diluted and applied to various objects that the birds come in contact with such as walls, cages, in the air and toys. Moreover, the present compositions in the form of solutions can also be applied directly on the birds.

The above-described compositions were discovered after detailed analysis of the chemical composition of secretions obtained from the uropygial gland in birds that had their young following them.

More particularly, this procedure involved swabbing the are around the uropygial glands of birds that had their young following them with a sterile compress and analyzing the chemical composition of the secretions. via gas chromatography/mass spectroscopy. This procedure is described in more detail in the examples below.

In order to fully illustrate the present invention and advantages thereof, the following specific examples are given, it being understood that the same are intended only as illustrative and in nowise limited.

EXAMPLES

Example 1

Isolation and Analysis to Identify Pheromones from Hens

Female hens that were followed by their young or not followed by their young were used in this example. The samples were obtained in female chickens followed by their young in a period of day 4, day 8, day 12 and day 35 after hatching. Another set of samples was taken from hens that were not followed by their young.

The hens were rubbed around the area of the uropygial gland or tail gland with sterilized compresses several times. The compress was immediately placed in a flask containing 10 ml of dichloromethane.

The compress was then deabsorbed in dichloromethane by agitating the flask several times. Five ml of the sample was taken out and subjected to evaporation down to 1 ml. using air.

Figure 2:
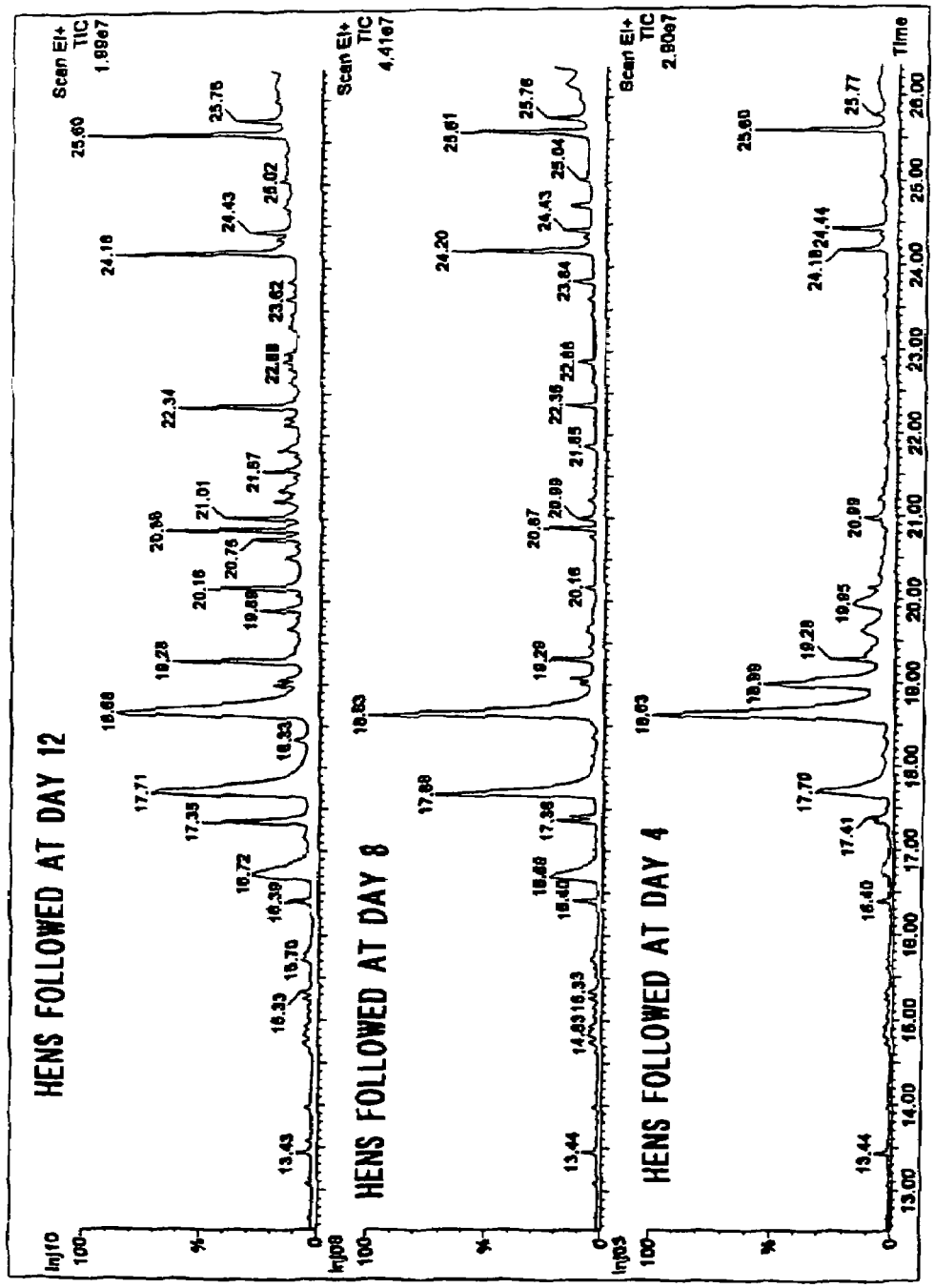
FIG. 2 are gas chromatograph/mass spectroscopy spectrum profiles of hens that were followed by their chicks at days 4, 8 and 12.

The samples were then subjected to grass chromatography/mass spectroscopy (GC/MS) using a Turbo Mass spectrometer made by Perkin Elmer. The detection was effectuated on impact using (EI+) at an energy of 70 eV at 180° C. A JW column type DB 5 MS having a length of 30 m (id=0.25 mm; film=0.25 μm at a split of 1/20 and a split/splitless of 45 seconds was used. 2.0 μl from each sample was injected. The spectrographic results from the GC/MS are shown in FIG. 1 and FIG. 2.

To confirm the structures of certain molecules obtained from the GC/MS analysis positive chemical Ionization (CI+) in methane was then performed to visualize the molecular peak (Molecular Mass). This method is well known in the art.

The results were analyzed using a data base to obtain the most probably spectrums. Data bases containing such data are well known in the art.

Table 1 below shows the results obtained from this example.

TABLE 1

| Composition | Familiar Name | Molecular Mass in g/mol | Time of Retention (minutes) |
|---|---|---|---|
| Dodecanoic Acid | Lauric acid | 200 | 13.1 |
| Hexadecanoic Acid | Palmitic acid | 256 | 17.4 |
| (Z,Z)-9,12-Octadadienoic Acid | Linoleic acid | 280 | 19.0 |
| (Z)-9-Octadecenoic Acid | Oleic acid | 282 | 19.1 |

After a complete analysis of the chromatographs, the avian appeasing pheromone was found to be constituted of the following composition in Table 2.

TABLE 2

| Composition | (wt %/wt %) |
|---|---|
| Lauric Acid | 12.3–13.7 |
| Palmitic Acid | 38.0–42.0 |
| Linoleic Acid | 32.3–35.7 |
| Oleic acid | 12.0–14.0 |

Example 2

Effect of Avian Appeasing Pheromone on Weight in Young Chicks

The following example was performed under the following breeders conditions:

Type of breeding: semi-open housing

Feeding: ad libitum for food and water with the food commonly used by all breeders to feed young chicks.

Two separate lots of young chicks were divided. Lot A received a dosage of 2% of the Avian Appeasing Pheromone comprising 13% lauric acid (w %/w %), 40% palmitic acid (w %/w %), 34% linoleic acid (w %/w %) and 13% oleic acid (w %/w %) which was placed in an electronic diffuser and placed above the young chicks in their housing. Lot B received a treatment with a placebo.

Prior to administering the avian appeasing pheromone or the placebo the young chicks were also grouped according to their weight; i.e., at day 0.

Figure 3:
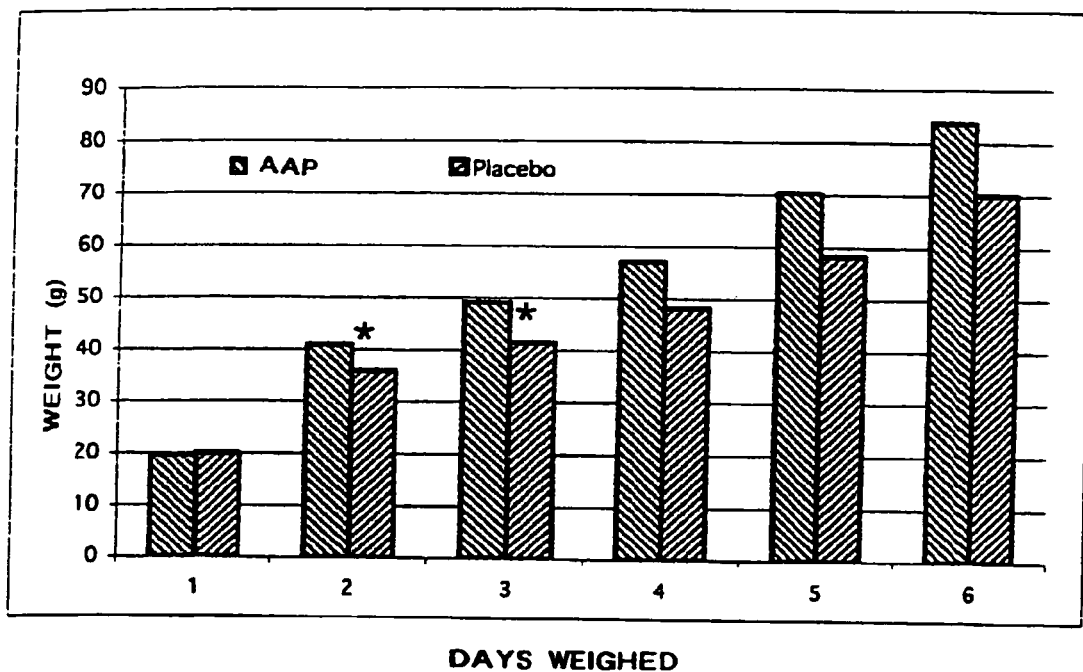
FIG. 3 is a bar graph showing that gain in weight of young chicks. ▧indicates that the chicks were treated with avian appeasing pheromone, while ▨indicates the chickens were treated with a placebo.
Figure 4:
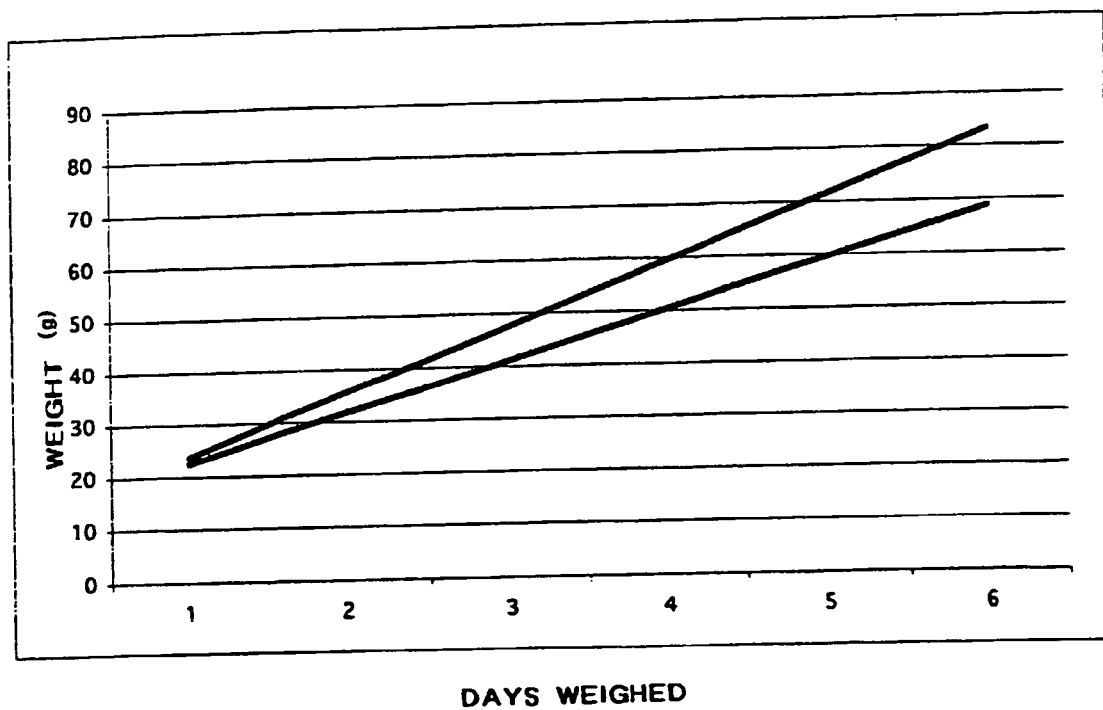
FIG. 4 is a graph showing the increase in weight gain in young chicks when administered avian appeasing pheromone (top line) in comparison with a placebo (bottom line).

The results are shown in FIGS. 3 and 4 where the groupings of the young chicks at day 0 were the same. From these Figures it was ascertained that with the treated Lot A there was an important weight gain in comparison to the placebo Lot B.

The weight gain is therefore more rapid when the avian appeasing pheromone is administered.

Example 3

The Effect of Avian Appeasing Pheromone in Chronic Stress Provoked in Hens and Roosters This example measured the influence of avian appeasing pheromone in hens and roosters subjected to hard and chronic stress.

The stressful conditions in which the hens and chickens were subjected to include bright lights, metallic noises, and electric shock. Two types of stressors were provoked each day for a period of 15 minutes in a random manner, which were identical for the two lots.

Lot A was treated with the avian appeasing pheromone (MP) comprising 13% lauric acid (w %/w %), 40% palmitic acid (w %/w %), 34% linoleic acid (w %/w %) and 13% oleic acid (w %/w %). Lot B was given a placebo. Several factors were then tested such as whether the hens or roosters gained weight, the changes in cortisol levels and the changes in T4 levels using standard tests for cortisol and T4, 8 days after the end of the experiment.

A difference in weight was not significantly observed. This could be because the stressors were too violent and that the pheromone could not prevent this type of violent stress.

Figure 5:
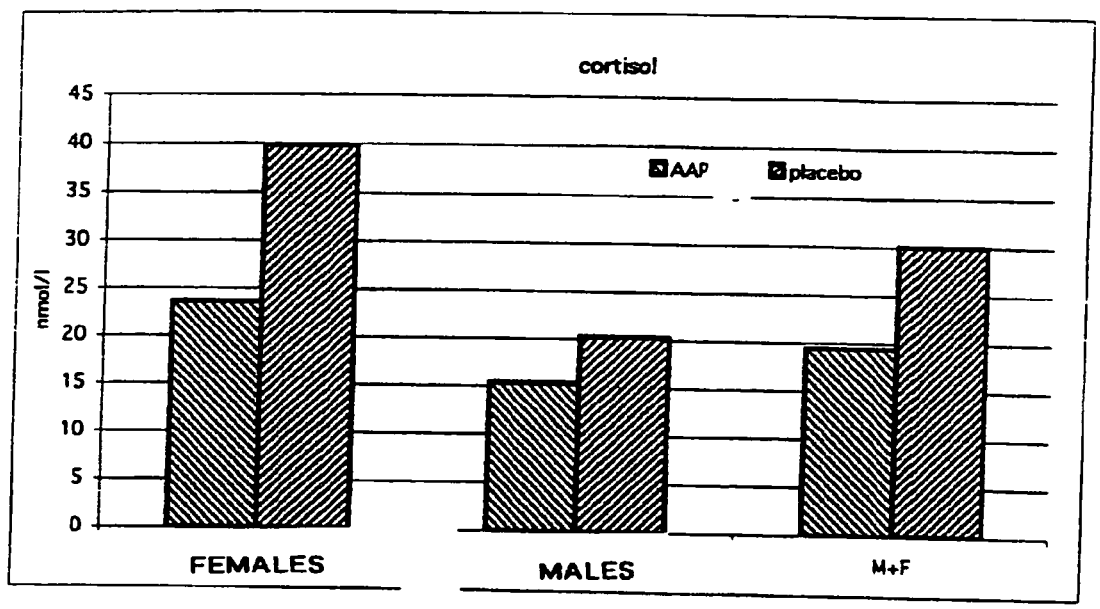
FIG. 5 is a bar graph showing the levels of cortisol in hens (Females) and roosters (Males) and males+females combined (M+F).

The endocrine results demonstrated an appeasing tendency on the individual animals, which were, administered the avian appeasing pheromone (A, B for cortisol—FIG. 5; $p=0.14$).

Idelman (1990),supra demonstrated that the phase of resistance to stress liberates hormones connected with the secretion of ACTH that stimulates cortisol, which cortisol is the hormone that is elevated the highest during stress. FIG. 5 illustrates that females are more sensitive to stress than males ($p=0.12$ for the females). Also the females have a more sensitive action to the avian appeasing pheromone; a decrease of about 50% of the level of cortisol before and after stress.

Figure 6:
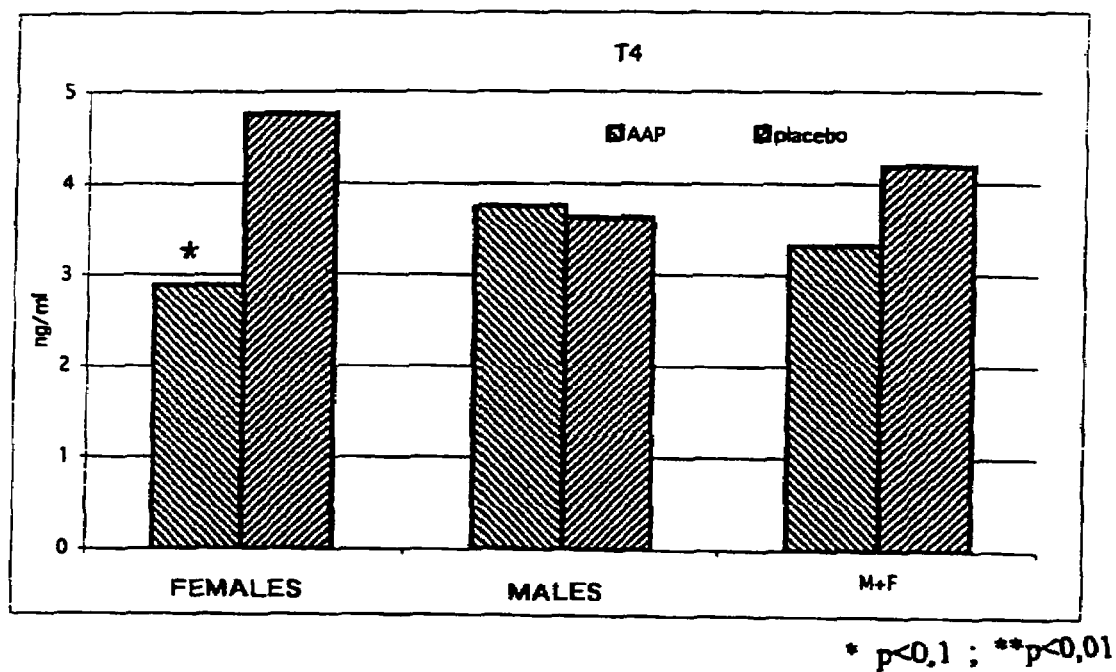
FIG. 6 is a bar graph showing the T4 levels in hens (Females) and roosters (Males) and males+females combined (M+F).

This was also confirmed by the level of T4 in females set forth in FIG. 6. Also these results prove that there is a significant difference between the nontreated and treated females, which is not the case for the males (FIG. 6; $p=0.08$).

Example 4

Avian Appeasing Pheromone and the Effect of Housing of the Chickens

This example was performed to determine whether housing the chickens had any effect on the results in double blind testing. Neither the person responsible for the project, nor the breeder knew the type of treatment in each housing.

The chickens were housed in two separate Lots of 2×13,000 chickens at a density of $18/m^2$ for each Lot. Lot 1 represents the first test, Lot 2 the second test, A and B treatments were as follows:

Lot 1 A1 (administered avian appeasing pheromone) vs. Lot B1 (placebo)

Lot 2: A2 (administered avian appeasing pheromone) vs. Lot B2 (placebo)

The avian appeasing pheromone that was administered comprised 13% lauric acid (w %/w %), 40% palmitic acid (w %/w %), 34% linoleic acid (w %/w %) and 13% oleic acid (w %/w %).

A solution of the avian appeasing pheromone titrated at 2% was the dosage used in this Example. This dosage was diffused with an electronic diffuser at a rate of $1/50\ m^2$.

Weight gain, cortisol levels, weight gain and indication of consumption levels and T4 levels were measured using standard tests for cortisol and T4 levels about 40 days after the end of the experiment.

It was further noted that the mean mortality rate was more elevated in one of the two housings of the chickens with respect to the other. This observation means that there is a possible "cross-over" when the placebo and the treatment are tested in only one housing.

The cortisol levels, T4 levels and weight were tested about 40 days after the initial testing.

The results from this example are as follows.

Figure 7:
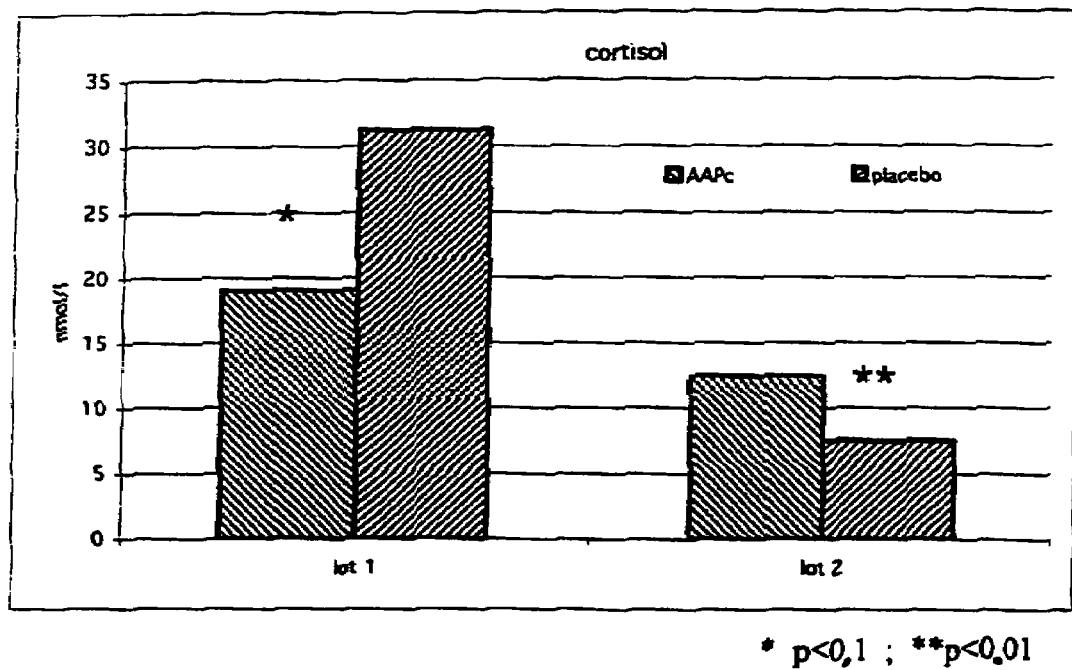
FIG. 7 is a bar graph showing the cortisol levels in chickens under different housing conditions. ▴indicates that the chickens were treated with avian appeasing pheromone, while ✶indicates the chickens were treated with a placebo.

The level of cortisol of B1 was significantly elevated in comparison with A1 (FIG. 7; $p=0.04$). This indicated that the mean state of stress was more pronounced in the birds in the lot non treated with the avian appeasing pheromone. One notices a significant difference in favor of lot B2 in comparison s with A2 (FIG. 7 $p=0.002$).

Figure 8:
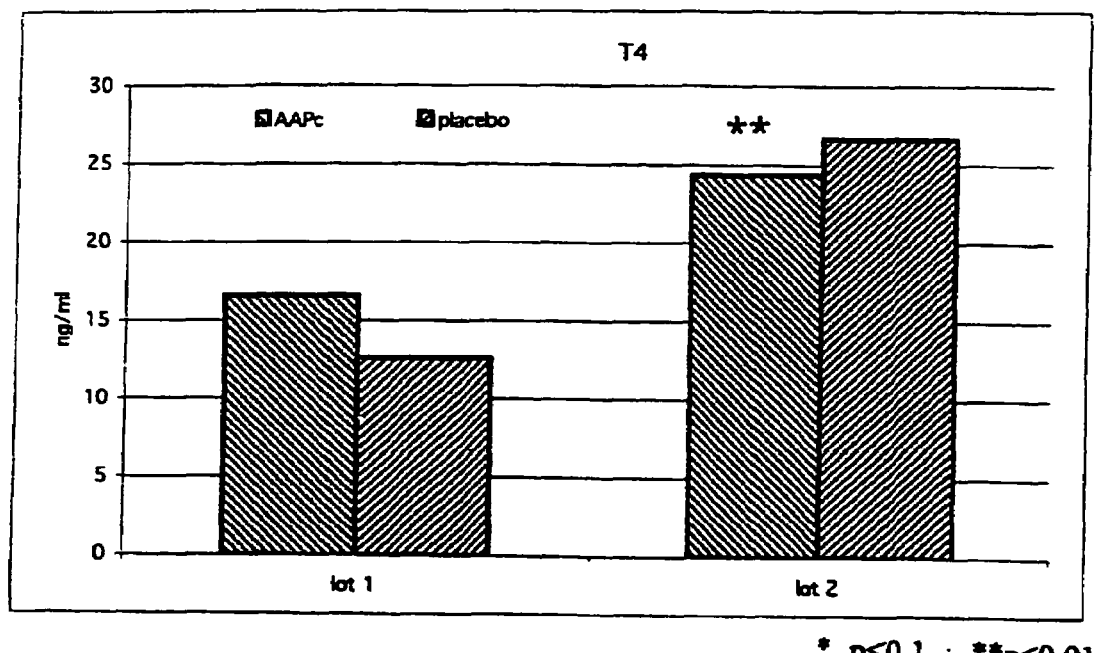
FIG. 8 is a bar graph showing the T4 levels in chickens under different housing conditions. ▴indicates that the chickens were treated with avian appeasing pheromone, while ✶indicates the chickens were treated with a placebo.

There was no significant difference between lots A1 and B1 in the T4 level. B2 had a level significantly higher than A2 with respect to the T4 level (FIG. 8; $p=0.006$).

Figure 9:
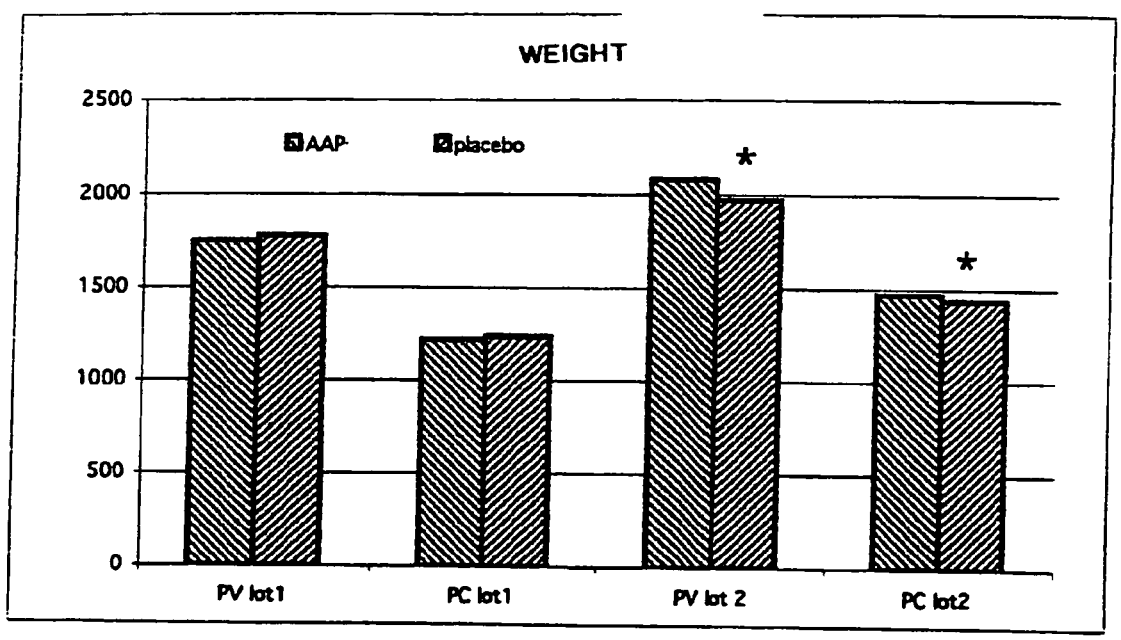
FIG. 9 is a bar graph showing the weight gain in chickens under different housing conditions. ▴indicates that the chickens were treated with avian appeasing pheromone, while ✶indicates the chickens were treated with a placebo.

For Lot 1 there was no significant weight difference between living weight (PV) or dead weight (PC). The animals in Lot A2 were significantly heavier that those in B2 (FIG. 9; $p=0.03$ and $p=0.06$, respectively for living weight and dead weight).

The weight gain and indication of consumption levels were equivalent (1.9 for indication of consumption) for the 4 different lots.

Figure 10:
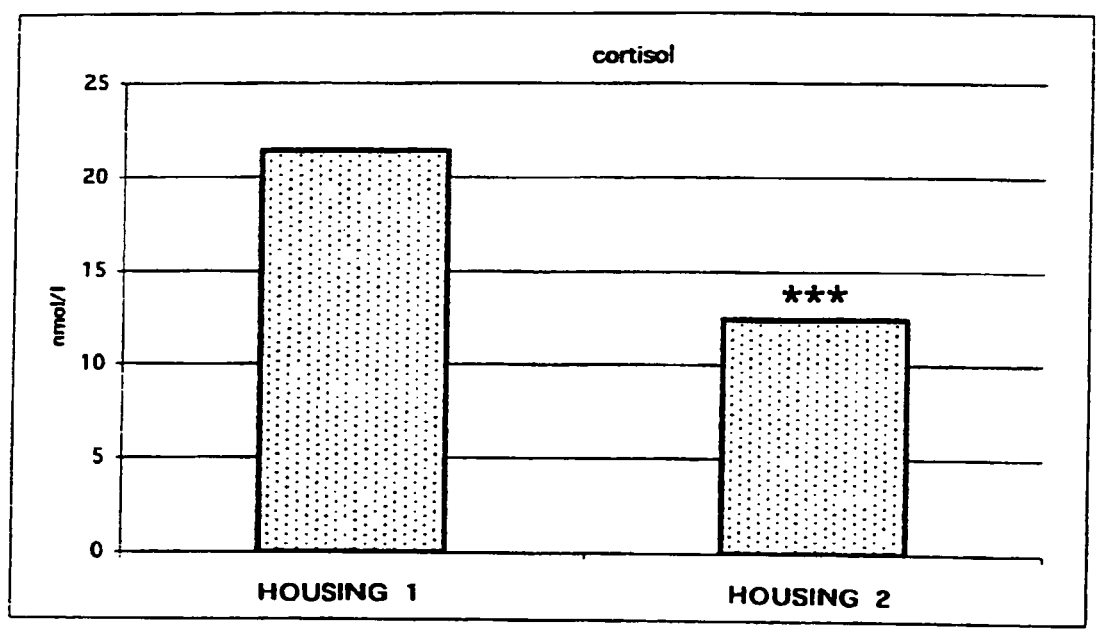
FIG. 10 is a bar graph showing the total cortisol levels under different housing conditions.

The results were also interpreted with respect to the effects of different housing of the chickens, which were tested. One finds the individuals in the same housing with a level of cortisol more elevated (FIG. 10; $p=0.003$). One notes no difference between A and B. There was no significant difference between A and B or in housing 1 or 2.

There was no significant difference between A and B, either in live weight or dead weight.

Therefore, the conclusions drawn were that there was no bias with housing of the chickens in this example.

Example 5

This protocol tests the influence of the avian appeasing pheromone on laying hens. The breeding techniques for laying hens are often stressful and cause a loss of eggs that are laid and also the squabbles between individual hens.

Various tests were performed in this example including zoological techniques, biological markers and sensitivity to mites on laying hens with or without administration of avian appeasing pheromone.

The following is a calendar of specific events that took place in this example:

Birth of the chicks: May year 1
Starting flock: 4 months after birth (year 1)
Starting feather pecking: 8 months after birth (year 2)
Treatment for mites (*Derrnanysuss* or *Omithonyssus*):9 months after birth (year 2)
Sampling for mites: 10 months after birth year 2
Sampling of blood: 10 months after birth year 2 and 11 months after birth year 2
Placing the diffusers with avian appeasing pheromone: 10 months after birth (year 2) and 11 months after birth year 2
Place eye glasses on hens: 10 months after birth year 2

Zoological technology was noted throughout the calendar of events described above using the following technical criteria: the rate of hens outside of their nests; the rate of hens in mass; the rate of mortality; and the alimentary consumption for those hens which were administered avian appeasing pheromone and those that were not administered avian appeasing pheromone (control).

There were no significant differences between the two groups. The results were equivalent with or without avian appeasing pheromone. The eye glasses did have an effect on the hens; the hens outside of their nests were less numerous and there were less number of declassified eggs.

Mites were also tested for during the course of this example. At day 0, the first diffusers of the avian appeasing pheromone were posed and the sampling of mites was effectuated. For the 12 samples that were taken, 5 samples permitted the identification of the species of mites in the breeding; 3 were utilized and placed in a mite culture and recuperated at the end of the internal experiment; and 4 served to test the sensitivity of parasites to the mites used.

On the 5 samples effectuated, 117 samples of parasites were identified. 76% (n=86) were identified as *Dermanyssus gallinae* (chicken mites) and 24% (n=28) were *Omithonyssus sylvianm* (Northern Fowl mites).

The quantity of mites found on the hens supports an important infestation to the breeder, with an internal sample of 2 it was estimated that the infestation between 5 and 6 out of a level of 8. (See, Devaney and Agutin (1987), which describes the scale of the number of *Orinthonyssus* on the skin just under the wing). The two last new infestations could not be obtained under the experimental conditions used.

One notes that the samples taken were effectuated only twp days after a treatment for mites. The breeder knew also that there was a strong infestation of mites and especially *Dermanyssus gallinae* (DG). The taken samples gave a final over-all global infestation of 5/8. This rate resulted in a sample of a size "professional" (1) that is considered 30 DG/cm$^2$ for a rate of maximum manifestation of 8. The rate 8/8 represents a stage of exsanguination with a rate of mortality near 100%. 5/8 represents a 3 to 5 DG/cm$^2$ level of infestation that is a stage intermediate in which treatment is obligatory to prevent an increase in mite infestation.

There were no dust mites found, which means that the mite treatment undertaken was efficient for dust mites. However, there was a large presence of parasitic mites just after mite treatment, which means that the parasitic mites most probably lost their sensitivity to the mite treatment that was used, which was tested for below.

Testing the sensitivity of the mites was next conducted. This test was performed in the population of mites with an in vitro system that verifies the sensitivity of the mite treatment utilized (Carbamate).

The parasites were thus exposed to a variety of concentrations of miticide. The dosage was determined by the value of the notice of dosage recommendation on the product. At this dose one does not obtain the LD 50 (50% of the mites exposed over a period of 24 hours are killed, nor the LD 100 (100% of mites are killed in a 24 hour period). The LD 50 was not obtained with a dose that was 8 times superior than that recommended. The LD 100 was not obtained with a does that was 32 times superior than that prescribed.

Under experimental conditions 2 lots (T1 and T2) were subjected to the tests. The T1 lot corresponded to a universal test, which is not authorized in breeding since Ivermectine was used. Lot 2 corresponded to a test made with Amitraze. For T1 and T2 the LD 100 was obtained with the doses prescribed on the notices of the products, in surroundings corresponding to the conditions of breeding. The results are shown in Table 3 below:

TABLE 3

| Active Material | Dose to obtain LD50 | Dose to obtain LD100 |
|---|---|---|
| Carbamate | 8 pd | >32 pd |
| Ivermectine (T1) | 1 pd | 1 pd |
| Amitraze (T2) | 1 pd | 1 pd | pd: prescribed dose

It was thus recommended that the active material for the mite treatment be changed, due to sensitivity as demonstrated above.

Blood tests were then performed as indicted in the calendar of events above. The different markers of stress were observed by the analysis effectuated with a blood sample. One observes an elevation with respect to Heterophiles/Lymphocytes (5) and also the variation in certain hormones such as (circulating T4, Cortisol and Prolactin (4)

The following methodology was used. Blood was drawn from the animals at the dates indicated in Table 4 below in two different types of tubes; one with no preservative (red top) and one with a preservative of EDTA (blue top).

The following physiological tests were done: hematocrit, blood cell counts and heterophiles/lymphocytes. The serum, after collection was conserved at −20° C. until all specimens were collected. The last were sent to a clinical laboratory for analysis for the rates of hormones of stress.

TABLE 4

| First blood samples drawn | Second blood samples drawn | Second blood samples drawn |
|---|---|---|
| March 7 | March 21 | April 19 |

The hematocrit was drawn in a tube containing the preservative EDTA and the results obtained are set forth in Table 5.

TABLE 5

| First blood samples drawn | Second blood samples drawn | Second blood samples drawn |
|---|---|---|
| 52% | 47% | 49% |

The normal physiological average for a hematocrit is 55%. As can be seen from the above results, there is a diminution in the hematorcrits, which signifies there is a decrease in red blood cells in the animal. This decrease indicates that the animals were injured in some manner. This blood loss is probably due to feather pecking in their tail area, which causes bad scaring and may lead to spots of blood on the eggs.

The white blood cell analysis showed a strong presence of granulocytes, which correlates with an infestation of parasites.

A leukocyte count was performed on the collected blood specimens and the results were presented using a ratio of heterophiles/lymphocytes. The results are presented in Table 4 below:

TABLE 6

| Drawn Blood samples | Mean | Variation | P value |
|---|---|---|---|
| $1^{st}$ vs. $2^{nd}$ | 2.49 | 0.14 | <0.0001* |
| $1^{st}$ vs. $3^{rd}$ | 0.69 | 0.07 | <0.0001 |
| $2^{nd}$ vs. $3^{rd}$ | 0.65 | 0.10 | 0.47 |

As can be seen from the above results, this study shows a mean value Of 2.49 for the first set of blood samples drawn and a fall of 60% for the second and third blood samples that were drawn. The statistical analysis indicated in the above Table 6 shows a difference between the first samples drawn and the second samples drawn and the first samples drawn and the third samples drawn but not a statistical difference between the second and third samples that were drawn. The mean average for breeders is 0.42±0.13 (3).

Figure 11:
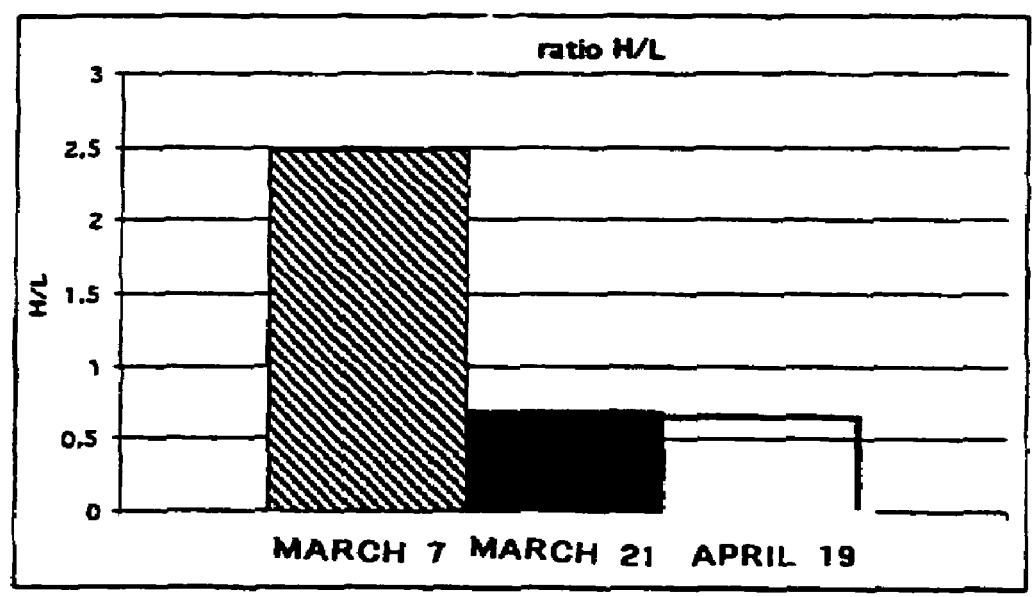
FIG. 11 is a bar graph showing the ratio of H/L on hens on different dates of the same year 2002.

The results are shown graphically in FIG. 11.

Conclusions

The avian appeasing pheromone decreases stress in avians. However, certain conditions must be maintained such that it works effectively. The avian appeasing pheromone should be used on young chicks immediately after they hatch.

The observations shown herein illustrates that even with an important stress such as intensive parasitism by chicken mites, the pheromone is able to decrease the induced stress. Therefore the pheromone composition of the present invention is effective even when the cause of stress endures.

Example 6

Animals and Breeding Conditions

Two identical buildings of 1200 m² each were utilized for this example. In each building, 24,000 "ROSS 308" chickens, divided in ⅔ males –⅓ females, were reared. The male and female chickens were separated for practical reasons. Male chickens were housed longer than female chickens since the males gain more weight in the last 10 days of production before slaughtering and thus it is economical more beneficial to the aviculturist to house male chickens for a longer period of time than the female chickens. On the day of the departure of the female chickens, the male chickens will occupy 100% of the area and are thus they free to roam the hen house. Males are generally sold carved, unlike females, which are sold in their entirety. In each one of the buildings, rearing conditions were strictly kept in a similar manner; i.e., the soil in the hen house was constituted of wood shavings (known as litter) distributed over the floor of both buildings, the chickens were fed ad libitum (food and water) and the light schedule was the same in both buildings. Natural daylight was used during daytime and artificial light was used at night. Six hours previous to the departure to the slaughterhouse, solid feeding of the chickens was stopped.

Treatment P010, an avian appeasing pheromone comprising a mixture of 13% lauric acid methylester (w %/w %), 40% palmitic acid methylester (w %/w %), 34.0% linoleic acid methylester (w %/w %) and 13.0 w % oleic acid methyl ester (w %/w %) was fabricated as a slow releasing block by methods known in the art that was protected by a plastic envelope pierced with holes. The treatment consisted of a passive diffusion of P010 into the local atmosphere.

Each block weighed 150 g and 18 blocks containing a concentration of 2% of the above avian appeasing pheromone were placed in the treated building (either P010 or a placebo). Treatment started on the day previous to the arrival of the chickens (noted as D0 or Day 0). On Day 29,(D29) the blocks containing P010 were replaced with new ones. In this trial, building 01 was treated with the placebo and building 02 with P010. The treated building will be referred to hereafter as "P010" and the other one "control" (placebo). The trial was run double blinded.

Transportation to the Slaughterhouse

The transportation of the chickens to the slaughterhouse was by van and the chickens were transported at midnight in containers with drawers containing 50 kg of live weight animals each.

The departure of the chickens to the slaughterhouse took place at midnight on the same day for each building; i.e., on Day 52 for male chickens and Day 40 for female chickens. These data are comparable to the National results (N.r.1) reported in ITAVI, (2001) Les syntheses economiques—performances techniques et couts de production (The Economic Synthesis-performance techniques and costs of production), which are Day 49 for male chickens versus Day 39 for female chickens.

Collected Data

Data Collected Prior to Transportation of the Chickens to the Slaughterhouse

Physiological tests were performed on blood samples taken from the chickens on the day of departure to the slaughterhouse. A total of 200 of these tests were performed (50 males and 50 females were tested for each building).

Blood was drawn from the chickens in both tubes containing EDTA and regular tubes not containing any chemical preservatives. Blood was collected at the wing vein of the chickens. Hematocrit/lymphocyte (H/L) ratio, hematocrit, glucose level and corticosterone level were measured. H/L was calculated using Mallacez cells on which 2×500 µl were spread over 50 squares (1 cm³). The calculation was computed using the cross up technique. Total lymphocyte population was then counted and the ratio was computed. The hematocrit was measured after centrifugation at 9000 m/s⁻² (3,500 rpm during 2 minutes) and expressed as the ratio of (total blood)/(cellular phase). The glucose level was measured using a Glucotrend®.

A Behavioral Test (BT) was also performed on the day in which the blood samples were taken. The Behavioral Test (BT) that was used is a derivative of the test of tonic immobility (TI) and is indicative of the fear reaction of the chickens when subjected to a situation simulating a predatory aggression. The Behavorial Test was performed as follows:

Each chicken was captured and placed on its back in a small hammock for a maximum of 60 seconds. Once the chicken was on its back, it is restrained gently by placing one hand touching its breast for 10 seconds and then released, while being stared at by another person eyes positioned at 1 meter, eye to eye.

Each of the physiological and behavioral results was obtained using the same chicken. Each chicken was captured, the Behavioral Test was performed, and then blood was drawn for the blood tests mentioned above. Glucose levels were computed immediately after the Behavioral Test.

Data Collected at the Slaughterhouse

At the slaughterhouse, several tests were undertaken concerning chicken yield. First, Live Weight (LW), Dead Weight (DW), Feed to Gain Ratio (FGR) and Performance Index (PI) were measured.

Live Weight (LW) was obtained by adding the overall weight of the chickens divided by the total number of chickens that were delivered by the breeder. The measurements were recorded separately for the male chickens and the female chickens.

Dead Weight (DW) was the measurement taken of the weight of each chicken individually. The weight was then classified in 100 g classes.

Feed to Gain Ratio (FDG) was the measurement taken for the total amount of food consumed by the chickens in each building for both male and female chickens.

Performance Index (PI) is the major index the chicken breeders took into account to evaluate performance. PI was calculated as follows: (Daily Weight Gain)/Feed to Gain Ratio (FGR).

The results from downgraded chickens which were suffocated, scratched and/or marked on their legs were also taken into account in the analysis. This criterion was calculated in percentage of the total delivered chickens to the slaughterhouse, excluding the percentage of Dead Weight (DW) for overall downgraded.

A procedure called "Table Yield" (TY) was also performed on standard chickens (n=10 per sex, from the same class of Dead Weight (DW): 1.9 kg for males and 1.2 kg for females). The Table Yield procedure evaluates animal yield; i.e., Fat, Fillet, Leg (meat), ratio Skin/Live Weight and Global Yield: (Skin+Leg)/Live Weight.

Finally, data concerning profitability were summarized to test the economical efficiency of P010 (Gross Margin or GM).

Statistical Analysis

Statistical analysis was performed using the Statview F-4.5® software. The data were analyzed by comparison of means and variances using the t-test and the Mann-Whitney U-test, when appropriate. Some data could not be statistically analyzed because of the lack of data and therefore statistical significance was not calculated. Nevertheless, some of the non-statistically analyzed results were shown because of their relation with other data.

Results of Example 6

TABLE 7

Mean of Dead Weight

|  | P010 | Control |
|---|---|---|
| Males | $2.22^a$ | $2.06^b$ |
| Females | $1.13^a$ | $1.09^b$ |

Means within a row with different superscript differ significantly ($p < 0.0001$, t-test)

TABLE 8

Downgraded animals - Males (% of animals except for Total: % of Dead Weight)

|  | P010 | Control |
|---|---|---|
| Suffocated (%) | 1.36 | 1.11* |
| Scratched | 8.00 | 22.00*** |
| Marked | 47.00 | 12.00*** |
| Total | 0.78 | 0.57** |

P values:
*$p < 0.05$,
**$p < 0.01$,
***$p < 0.001$ (t-test)

TABLE 9

Downgraded animals - Females (% of animals except for Total: % of Dead Weight)

|  | P010 | Control |
|---|---|---|
| Suffocated (%) | 3.25 | 6.36*** |
| Scratched | 10.00 | 19.00*** |
| Marked | 8.00 | 4.00*** |
| Total | 0.21 | 0.26 |

P values:
*$p < 0.05$,
**$p < 0.01$,
***$p < 0.001$ (t-test)

TABLE 10

Physiological results - Males

|  | P010 | Control |
|---|---|---|
| Heterophile/Lymphocyte | 0.81 | $1.11^{uu}$ |
| Albumin/Globulin | 0.44 | $0.56^{uu}$ |
| Hematocrit (%) | 44.3 | 44.1 |
| Glucose (mg/dl) | 205 | 197** |
| Corticosterone (ng/ml) | 2.64 | 3.40* |

P values:
*$p < 0.05$,
**$p < 0.01$,
***$p < 0.001$ (t-test)/
$^u p < 0.05$,
$^{uu} p < 0.01$,
$^{uuu} p < 0.001$ (U-test)

TABLE 11

Physiological results - Females

|  | P010 | Control |
|---|---|---|
| Heterophile/Lymphocyte | 0.77 | 0.85*** |
| Albumin/Globulin | 0.91 | 0.82 |
| Hematocrit (%) | 49.6 | 49.5 |
| Glucose (mg/dl) | 199 | 203 |
| Corticosterone (ng/ml) | 2.27 | 2.35 |

P values: *$p < 0.05$, $p < 0.01$, *$p < 0.001$ (t-test) / $^u p < 0.05$, $^{uu} p < 0.01$, $^{uuu} p < 0.001$ (U-test)

Analysis of the Results

The difference between control and P010 was significant for Dead Weight (DW) for both male chickens and female chickens. The control chickens were lighter compared to P010 treated chickens ($p<0.0001$, (see, Table 7, above). Final Live Weight (LW) was lower in the control group compared to P010 for both male and female chickens (a mean of 2.84 kg (control) versus 3.08 kg (treated) and 1.60 (control) versus 1.69 kg (treated), respectively). P010 male chickens were heavier compared to those found in the National results (N.r.1) (2.85 kg). Food to Gain Ratio (FGR) was slightly higher in the P010 building (1.96 (treated) versus 1.90 (control) respectively), which represents the National mean as described in Le Douarin P. Enquete technico economique. Reussir Aviculture 83: 24-24 (2003)). However, the Performance Index (PI) was higher for the P010 treated chickens compared to the control chickens (2.49 (treated) versus 2.40 (control), which means that Daily Weight Gain (DWG) was higher for the P010 chickens.

Even though some of this data could not be statistically compared, they are helpful in understanding the differences in Dead Weight (DW). The National results value (N.r.2) for Live Weight (LW) is 2.35 kg as set forth in Le Douarin P (2003), supra The results obtained herein for the Live Weight of chickens was 2.38 kg for P010 and 2.20 kg for the control chickens. One notes that the control is slightly under the National results 2 value which is not the case for P010. This observation can account for the difference shown in the Dead Weight (DW) since it can be considered that there is a correlation between the Dead Weight (DW) and the Live Weight (LW) (Feddes J. J. R., E. J. Emmanuel, M. J. Zuidhof, *Poult. Sci.* 81: 774-779 (2002).

Moreover, it is logical that a higher Daily Weight Gain (DWG) leads to an increased final weight, without considering the Feed to Gain Ratio (FGR). This gives a justification to the great importance given to the Performance Index (PI).

Total downgraded P010 male chickens (see, Table 8, above) represented 0.78% of the Dead Weight (DW), compared to 0.57% for the total downgraded control chickens ($p<0.01$). This is due to the higher level of marked legs for the P010 treated chickens (47% versus 12%, $p<0.001$). However, percentage of both suffocated and scratched chickens are lower in the P010 treated chickens as evidenced by the values of 1.36% (male treated) versus 1.11% male controls for suffocation and 8% (male treated) versus 22% (male control) ($p<0.001$) for scratched chickens.

Results concerning the female chickens are comparable to those of the male chickens (see, Table 9, above). The results showed a significantly higher number of marked legs for female chickens treated with P010 (8% (treated) versus 4% (control) $p<0.001$), but a lower number of P010 treated female chickens suffocated (3.25% (treated) versus 6.36% (control), $p<0.001$) and were scratched (10% (treated) versus 19% (control), $p<0.001$) for the P010 group.

Nevertheless, no significant difference was found for total downgraded Dead Weight (DW) for the chickens in this trial. The Total downgraded P010 treated chickens were under the National results 2 value of 0.96% as set forth in Le Douarin P (2003), supra.

Although the trial took place in clean buildings, some slaughterhouses utilize a system of grading of marked legs that correlates with too 5 humid litter on the hen housing floor (LEJAS I., La France Agricole. (Fev.(February) 2003)). For example, the threshold of 40% of marked chicken legs is an indication that the flock is affected and 80% is an indication that the flock is "over-affected". In this trial, P010 male chickens can be considered as affected. This correlates with the fact that litter samples showed a higher level of moisture in one of the buildings, compared to the control.

Although the total amount of water utilized by the chickens for each building was not undertaken, it can be assumed that the treated P010 chickens consumed more water compared to the untreated control chickens, which agrees with the difference in Feed to Gain Ratio (FGR). Because the male chickens is stayed longer in the hen house before slaughtering, it is logical that they are more affected by the litter quality. Finally, it is because total downgraded chickens are represented in the calculation of all these criterion that the results appear to be lower, even if all other criterion (except marked legs) are good.

Concerning Table Yield (TY) none of the results observed were statistically different for both male chickens and female chickens. However, it was observed that P010 chickens seemed to have had more meat compared to the control chickens.

The two observed groups showed differences among sexes for the physiological results (see Table 4 and Table 5, above). Indeed, the H/L ratio was significantly lower for the P010 chickens ($p<0.01$) and is the unique parameter that showed a difference for female chickens among the groups. Concerning the male chickens, the Corticosterone level was higher for the control ($p<0.05$), but the glucose level was lower ($p<0.01$) for this same control group. It is interesting to observe that these results tend to show that male chickens have a level of stress that is different among the groups. The case is less for the female chickens, except for the HIL ratio, which tends to represent a social stress (Campo J. L., Davila S. G., *Poult. Sci.* 81: 1637-1639 (2002)). Once again, the fact that the departure of males took place 12 days after the females can be an explanation.

Concerning the hematocrit, the groups are comparable, and the data are in accordance with the literature (Fisher T. M., *Blood Cells.* 4: 453-461 (1978)). Data from physiological results could be observed in parallel with those of Table Yield (TY). Indeed, poultry exposed to a stressor tend to stock fat and thus are leaner; i.e., they have less meat (Leclerc B., Guy, G., Rideaux, F. *Reprod. Nutr. Dev.* 28: 931-937 (1988)). Elevation of the Corticosterone levels seems to diminish the capacity of protein metabolism (Grizard J., et al., *Nutr. Research Rev.* 8: 67-91(1995)). The male poultry glucose scores appeared to be ambiguous, even if they are similar to the ones in literature (Padilha J. F. C., Influence of heat on energy metabolism and its regulation on broilers. French Thesis for PhD. Tours University, 205 pages 1995)). Indeed, it can be argued that the P010 chickens were "very reactive" which could also explain the differences in fatness since there is a lower capture of glucose by muscles, which tends to lead to a higher lipids storage rate (Bray G. A., York, D. A. *Physiol. Reviews.* 59: 719-809 (1979).). Thus, it can be concluded that stress leads to a poor carcass quality because of an elevation of lactic acid production that generates a low pH meat (Alvarado C. Z., Sams A. R., *Poult. Sci.* 81: 1365-1370 (2002)).

No differences among groups or the sexes could be shown using the Behavioral Test (BT). This test gave mean of 39.6 seconds for male poultry and 41.2 seconds for female poultry. Compared to a referenced test (Riedstra B., Groothuis, N. *Appl. Anim. Behav. Sci.* 77: 127-138 (2002)), it could be argued that this test was not performed long enough to observe a real difference between the poultry. The Behavorial Test (BT) was performed in this trial so that a quick result could be obtained by the breeder to grasp the stress level of the flock.

Finally, the Gross Margin (GM) was computed for each building and found that the margin chicken/food was higher in the P010 building by 4.8%.

In conclusion, the P010 product reducers stress in chickens and it economically beneficial to the aviculturist as evidenced by the above results.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

What is claimed is:

1. A composition comprising an avian appeasing pheromone comprising lauric acid, palmitic acid, linoleic acid and oleic acid and/or derivatives thereof and/or isomers thereof, as well as mixtures of one or more of these fatty acids with one or more of their derivatives and/or one or more of their isomers.

2. The composition according to claim 1, wherein said composition comprises an avian appeasing pheromone comprising about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

3. The composition according to claim 1, wherein said derivatives are esters, salts, alcohols, ketones, ethers, aldehydes, sterols and amides of lauric acid, palmitic acid, linoleic acid and oleic acid.

4. The composition according to claim 1, further comprising a nontoxic filler or a solid excipient.

5. The composition according to claim 4, wherein said nontoxic filler is selected from the group of fatty acids, alcohols, amines, squalene and glycerol.

6. A solution comprising an avian appeasing pheromone comprising lauric acid, palmitic acid, linoleic acid and oleic acid and derivatives thereof and a solvent.

7. The solution according to claim 6, wherein said solution comprises an avian appeasing pheromone comprising an avian appeasing pheromone comprising about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

8. The solution according to claim 6, wherein said solvent is alcohol and propylene glycol.

9. The solution according to claim 8, wherein said solution is in the form of a spray, a shampoo, an aerosol, is microencapsulated, is in a slow release matrix or in a diffuser.

10. The solution according to claim 9, wherein said diffuser is an electric diffuser.

11. A process for the treatment of stress in an avian said process comprising administering to an avian in need of such treatment a composition according to claim 1.

12. The process according to claim 11, wherein said composition comprises an avian appeasing pheromone comprising about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

13. The process according to claim 11, wherein said composition is in solution and is administered by applying said solution to walls, on the feathers or skin of an avian, in the air or on toys.

14. A process of treating weight loss in an avian, said process comprising administering to an avian in need of such treatment an avian appeasing pheromonal composition according to claim 1.

15. The process according to claim 14, wherein said composition comprises an avian appeasing pheromone comprising about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

16. The process according to claim 14, wherein said composition is in solution and is administered by applying said solution to walls, on the feathers or skin of an avian, in the air or on toys.

17. A process of treating a domestic avian during transportation to eliminate their anxiety, said process comprising administering to an avian in need of such treatment an avian appeasing pheromonal composition according to claim 1.

18. The process according to claim 17, wherein said composition comprises an avian appeasing pheromone comprising about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

19. The process according to claim 17, wherein said composition is in solution and is administered by applying said solution to walls, on the feathers or skin of an avian, in the air or on toys.

20. A process to improve feed conversion in an avian comprising administering to an avian in need of such treatment an avian appeasing pheromonal composition according to claim 1.

21. The process according to claim 20, wherein said composition comprises an avian appeasing pheromone comprising about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers.

22. The process according to claim 20, wherein said composition is in solution and is administered by applying said solution to walls, on the feathers or skin of an avian, in the air or on toys.

23. A composition comprising an avian appeasing pheromone comprising about 12.3 to 13.7 (w %/w %) of lauric acid, about 38.0 to 42.0 (w %/w %) palmitic acid, about 32.3 to 35.7 (w %/w %) linoleic acid and about 12.0 to 14.0 (w %/w %) oleic acid and/or derivatives thereof and/or isomers thereof, as well as mixtures of one or more of these fatty acids with one or more of their derivatives and/or one or more of their isomers, wherein said derivatives are esters, salts, alcohols, ketones, ethers, aldehydes, sterols and amides of lauric acid, palmitic acid, linoleic acid and oleic acid.

* * * * *